US009775815B2

(12) United States Patent
Schattka et al.

(10) Patent No.: US 9,775,815 B2
(45) Date of Patent: Oct. 3, 2017

(54) GASTRIC RESISTANT PHARMACEUTICAL OR NUTRACEUTICAL COMPOSITION WITH RESISTANCE AGAINST THE INFLUENCE OF ETHANOL

(75) Inventors: Jan Hendrik Schattka, Darmstadt (DE); Christian Meier, Darmstadt (DE); Herbert Jung, Karlstein (DE); Hedi Krachtus, Pfungstadt (DE); Jessica Del Rosario Ferrand, Eppertshausen (DE)

(73) Assignee: Evonik Roehm GmbH, Darmstadt (DE)

( * ) Notice: Subject to any disclaimer, the term of this patent is extended or adjusted under 35 U.S.C. 154(b) by 594 days.

(21) Appl. No.: 14/114,752

(22) PCT Filed: Jun. 12, 2012

(86) PCT No.: PCT/EP2012/061051
§ 371 (c)(1),
(2), (4) Date: Oct. 30, 2013

(87) PCT Pub. No.: WO2012/171884
PCT Pub. Date: Dec. 20, 2012

(65) Prior Publication Data
US 2014/0141092 A1    May 22, 2014

(30) Foreign Application Priority Data

Jun. 17, 2011 (WO) .................. PCT/EP2011/060098

(51) Int. Cl.
*A61K 9/50* (2006.01)
*A61K 9/28* (2006.01)

(52) U.S. Cl.
CPC .......... *A61K 9/5026* (2013.01); *A61K 9/2846* (2013.01); *A61K 9/5078* (2013.01)

(58) Field of Classification Search
None
See application file for complete search history.

(56) References Cited

U.S. PATENT DOCUMENTS

| 5,705,189 A | 1/1998 | Lehmann et al. | |
| 9,668,977 B2* | 6/2017 | Schattka | A61K 9/5026 |
| 2004/0039356 A1* | 2/2004 | Maki | A61K 31/565 604/307 |
| 2005/0084541 A1* | 4/2005 | Nandi | A61K 9/1652 424/490 |
| 2005/0152977 A1* | 7/2005 | Petereit | A61K 9/2846 424/471 |
| 2006/0204576 A1 | 9/2006 | Petereit et al. | |
| 2008/0064821 A1 | 3/2008 | Mentak et al. | |
| 2010/0221324 A1 | 9/2010 | Petereit et al. | |
| 2010/0226978 A1 | 9/2010 | Petereit et al. | |
| 2011/0217383 A1 | 9/2011 | Baer et al. | |
| 2011/0229562 A1 | 9/2011 | Baer et al. | |
| 2014/0079792 A1 | 3/2014 | Schattka et al. | |
| 2014/0086997 A1 | 3/2014 | Nollenberger et al. | |
| 2014/0141092 A1 | 5/2014 | Schattka et al. | |

FOREIGN PATENT DOCUMENTS

| CN | 1688295 A | 10/2005 | |
| CN | 101050256 A | 10/2007 | |
| CN | 101801357 A | 8/2010 | |
| DE | WO 2010034342 A1 * | 4/2010 | ........... A61K 9/5078 |
| JP | 2004-51578 A | 2/2004 | |
| JP | 2006-524643 A | 11/2006 | |
| JP | 2007-518670 A | 7/2007 | |
| JP | 2010-539196 A | 12/2010 | |
| JP | 2010-539197 A | 12/2010 | |
| WO | 2009 036811 | 3/2009 | |
| WO | 2010 034342 | 4/2010 | |
| WO | 2010 034344 | 4/2010 | |

OTHER PUBLICATIONS

Combined Chinese Office Action and Search Report issued Dec. 26, 2014 in Patent Application No. 201280021621.7 (with English language translation).
U.S. Appl. No. 14/114,752, filed Oct 30, 2013, Schattka, et al.
U.S. Appl. No. 14/118,078, filed Nov. 15, 2013, Nollenberger, et al.
U.S. Appl. No. 14/115,632, filed Nov. 5, 2013, Schattka, et al.
International Search Report Issued Jul. 27, 2012 in PCT/EP12/61051 Filed Jun. 12, 2012.
Written Opinion of The International Searching Authority Issued Jul. 27, 2012 in PCT/EP12/61051 Filed Jun. 12, 2012.
Japanese Office Action issued Feb. 1, 2016 in Patent Application No. 2014-515149 (with English language translation).
Tadao Ida, et al., "Studies on Protective Coating XV, Enteric Coating, (3) Internal Plasticized Acrylic and Methacrylic Acid Derivatives" vol. 82, No. 7, 1962, pp. 1012-1016, Japanese with partial English.
Russian Office Action issued May 30, 2016 in Patent Application No. 2014101230 (with English Translation).
I.V. Pokrovskiy et al., "Encycklopedicheskiy slovar medizinskih terminov", Izdanie vtoroe Moskva, "Medizina", 2001, str. 531 (with Partial English Translation) and str. 603 (with Partial English Translation).
I.V. Chueshov, "Promyshlennaya technologiya lekarstv", tom 1, Charkov, Izdatel'stvo NFAU, 2002, str. 24, 1-2 absatz (with Partial English Translation).

* cited by examiner

*Primary Examiner* — Isaac Shomer
(74) *Attorney, Agent, or Firm* — Oblon, McClelland, Maier & Neustadt, L.L.P.

(57) ABSTRACT

The invention discloses a gastric resistant pharmaceutical or nutraceutical composition, comprising a core, comprising a pharmaceutical or nutraceutical active ingredient and a gastric resistant coating layer onto the core, wherein the gastric resistant coating layer comprises at least 30% by weight of a (meth)acrylate copolymer comprising polymerized units of 10 to 40% by weight of acrylic or methacrylic acid, 10 to 80% by weight of a $C_4$- to $C_{18}$-alkyl ester of acrylic or methacrylic acid and optionally 0 to 60% by weight of another vinylic monomer, whereby the release of the pharmaceutical or nutraceutical active ingredient is not more than 10% under in-vitro conditions at pH 1.2 after 2 hours in medium according to USP with and without the addition of 20% (v/v) ethanol.

12 Claims, No Drawings

GASTRIC RESISTANT PHARMACEUTICAL OR NUTRACEUTICAL COMPOSITION WITH RESISTANCE AGAINST THE INFLUENCE OF ETHANOL

FIELD OF THE INVENTION

The present invention is concerned with a gastric resistant pharmaceutical or nutraceutical composition, comprising a core, comprising a pharmaceutical or nutraceutical active ingredient and a gastric resistant coating layer onto the core, whereby the release of the pharmaceutical or nutraceutical active ingredient is not more than 10% under in-vitro conditions at pH 1.2 after 2 hours in medium according to USP with and without the addition of 20% (v/v) ethanol.

TECHNICAL BACKGROUND (Meth)acrylate copolymers containing anionic groups are for instance disclosed in EP0704208B1, EP0704207A2, WO03/072087A1, WO2004/096185A1.

Controlled release pharmaceutical compositions with resistance against the influence of ethanol employing a coating comprising neutral vinyl polymers and excipients are known from WO2010/105672A1.

Controlled release pharmaceutical compositions with resistance against the influence of ethanol employing a coating comprising a polymer mixture and excipients are known from WO2010/105673A1.

PH-dependent controlled release pharmaceutical composition for narcotic drugs (opioids) with decreased susceptibility to the influence of ethanol on the release of active compound are known from WO2009/036812A1 and WO2010034342A1.

PH-dependent controlled release pharmaceutical compositions for drugs that are not opioids with decreased susceptibility to the influence of ethanol on the release of active compound are known from WO2009/036811A1 and WO2010034344A1. WO2008/049657 describes the use of gastric resistant (meth)acrylate copolymers in retarded oral dosage forms as matrix formers for the active ingredient included in order to minimize the effect of acceleration or deceleration of the active ingredient release by the influence of ethanol under in-vitro conditions.

GENERAL DEFINITIONS

Singular forms like "a", "an", "the" or "another" as used in the description or in the claims shall be understood as to include the plural of the defined subject within the given definition or limits as well if not stated explicitly otherwise. For instance the singular term "a (meth)acrylate copolymer" or "the (meth)acrylate copolymer" shall have the meaning of one or more (meth)acrylate copolymers within the given definition or limits of the monomer composition. Thus mixtures of different (meth)acrylate copolymers within the given definition or limits of the monomer composition are included in the sense of the invention. Singular terms like "a $C_4$- to $C_{18}$-alkyl ester of acrylic or methacrylic acid" or "another vinylic monomer" shall be understood in the same way to include one or more of these monomers.

Preferably the monomer ratios for copolymers disclosed herein add up to 100% by weight.

Problem and Solution

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for gastric resistant pharmaceutical or nutraceutical compositions, such that their mode of action is affected as little as possible by the presence of ethanol.

Conventional gastric resistant pharmaceutical or nutraceutical compositions if coated or uncoated are usually not resistant to alcohol at all. Therefore one problem of the present invention was to provide gastric resistant pharmaceutical or nutraceutical compositions which are resistant against the influence of ethanol.

Especially there is a problem for gastric resistant or enteric formulated compositions. These kinds of formulations are usually coated with a gastric resistant coating layer (enteric coating layer) onto the core which has the function that the release of the pharmaceutical or nutraceutical active ingredient in the stomach, respectively at pH 1.2 for 2 hours according to USP, shall not exceed 10, 8 or maybe 5%. This function ensures that acid-sensitive pharmaceutical or nutraceutical active ingredients are protected against inactivation and that pharmaceutical or nutraceutical active ingredients which may be irritate the stomach mucosa are not set free in too high amounts. On the other hand in many cases the release of the pharmaceutical or nutraceutical active ingredient in the intestine, respectively at pH 6.8 for one hour or less according to the USP method, is designed to exceed at least 50, 60, 80% or more. The presence of ethanol in concentrations of 20, 30 or 40% (volume/volume) in the gastric fluid usually leads to an increase to the release rates in the stomach. Due to distribution effect the effect of ingested ethanol is in the intestine not of that importance as in the stomach. Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

The several problems as discussed are solved by a gastric resistant pharmaceutical or nutraceutical composition, comprising a core, comprising a pharmaceutical or nutraceutical active ingredient and a gastric resistant coating layer onto the core, wherein the gastric resistant coating layer comprises, essentially comprises or contains at least 30% by weight of a (meth)acrylate copolymer comprising polymerized units of
10 to 40% by weight of acrylic or methacrylic acid
10 to 80% by weight of a $C_4$- to $C_{18}$-alkyl ester of acrylic or methacrylic acid and optionally
0 to 60% by weight of another vinylic monomer, whereby the release of the pharmaceutical or nutraceutical active ingredient is not more than 10% under in-vitro conditions at pH 1.2 after 2 hours in medium according to USP with and without the addition of 20% (v/v) ethanol.

DETAILED DESCRIPTION OF THE INVENTION

The invention is concerned with a gastric resistant pharmaceutical or nutraceutical composition, comprising a core, comprising a pharmaceutical or nutraceutical active ingredient and a gastric resistant coating layer onto the core.

The Gastric Resistant Coating Layer

The gastric resistant coating layer comprises at least 30, at least 40, at least 50, at least 60, at least 70, at least 80, at least 90 or 100% by weight of a (meth)acrylate copolymer comprising polymerized units of the (meth)acrylate copolymer as claimed.

The (Meth)Acrylate Copolymer

Preferably the monomer ratios for copolymers disclosed herein add up to 100% by weight.

The (meth)acrylate copolymer is comprising, essentially comprising, containing or consisting of polymerized units of
10 to 40% by weight of acrylic or methacrylic acid
10 to 80% by weight of a $C_4$- to $C_{18}$-alkyl ester of acrylic or methacrylic acid and optionally
0 to 60% by weight of another vinylic monomer.

$C_4$- to $C_{18}$-alkyl ester of acrylic or methacrylic acid are preferably chosen from n-butyl methacrylate, 2-ethylhexyl acrylate, 2-ethylhexyl methacrylate, isodecyl methacrylate and lauryl methacrylate.

Another vinylic monomer is a monomer which is not acrylic or methacrylic acid or a $C_4$- to $C_{18}$-alkyl ester of acrylic or methacrylic acid. Another vinylic monomer may be preferably $C_1$- to $C_3$-alkyl ester of acrylic or methacrylic acid, which are methyl acrylate, ethyl acrylate, propyl acrylate, methyl methacrylate, ethyl methacrylate or propyl methacrylate. Another vinylic monomer may be hydroxyethyl methacrylate, hydroxypropyl methacrylate, poly(ethylenglycol)methylether acrylat, poly(ethylenglycol)methylether methacrylat, poly(propylenglycol)methylether acrylat, poly(propylenglycol)methylether methacrylat or styrene.

Preferably the (meth)acrylate copolymer is comprising, essentially comprising or containing polymerized units of
10 to 40% by weight of acrylic or methacrylic acid
10 to 50% by weight of ethyl acrylate
10 to 80% by weight of a $C_4$- to $C_{18}$-alkyl ester of acrylic or methacrylic acid and optionally
0 to 20 by weight of methyl methacrylate.

Preferably the (meth)acrylate copolymer is comprising, essentially comprising or containing polymerized units of
20 to 40% by weight of methacrylic acid,
20 to 40% by weight of n-butyl methacrylate and
30 to 50% by weight of ethyl acrylate Preferably the (meth)acrylate copolymer is comprising, essentially comprising or containing polymerized units of
20 to 40% by weight of methacrylic acid,
30 to 50% by weight of 2-ethylhexyl acrylate,
15 to 40% by weight of ethyl acrylate and optionally
0 to 20% by weight of methyl methacrylate.

Preferably the (meth)acrylate copolymer is comprising, essentially comprising or containing polymerized units of
10 to 40% by weight of methacrylic acid,
20 to 70% by weight of 2-ethylhexyl methacrylate and
10 to 50% by weight of ethyl acrylate.

Preferably the (meth)acrylate copolymer is comprising, essentially comprising or containing polymerized units of
20 to 40% by weight of methacrylic acid,
20 to 50% by weight of 2-ethylhexyl methacrylate and
20 to 50% by weight of ethyl acrylate.

Preferably the (meth)acrylate copolymer is comprising, essentially comprising or containing polymerized units of
10 to 35% by weight of methacrylic acid,
40 to 70% by weight of 2-ethylhexyl methacrylate and
10 to 30% by weight of ethyl acrylate.

Preferably the (meth)acrylate copolymer is comprising, essentially comprising or containing polymerized units of
20 to 40% by weight of methacrylic acid,
20 to 40% by weight of isodecyl methacrylate and
40 to 50% by weight of ethyl acrylate.

Preferably the (meth)acrylate copolymer is comprising, essentially comprising or containing polymerized units of
20 to 40% by weight of methacrylic acid,
20 to 40% by weight of lauryl methacrylate and
30 to 50% by weight of ethyl acrylate.

Process for Preparing the (Meth)Acrylate Copolymer

The (meth)acrylate copolymer may be produced by radical polymerisation of the monomers in the presence of polymerisation initiators.

A chain transfer agent may be added to improve the process stability and reproducibility of the molecular weight (Mw). A usual chain transfer agent amount may be 0.05 to 1% by weight. A typical chain transfer agent may be for example thioglycolic acid 2-ethyl hexyl ester (TGEH) or n-dodecyl mercaptane (nDDM). However the chain transfer agent may be omitted in many cases, without affecting the properties according to the invention.

Preparation methods for the (co)polymers are known to the expert in the field. Typically emulsion polymerization, solution polymerization or bulk polymerization will be applied; the preferred preparation of the (co)polymers is by emulsion polymerization.

If emulsion polymerization is used, the operation may advantageously be carried out by the monomer emulsion feed process or the monomer feed process, respectively. For this, water is heated to the reaction temperature in the polymerization reactor. Surfactants and/or initiators may be added at this stage. Then—depending on the mode of operation—the monomer, a monomer mixture or a an emulsion of either are fed to the reactor. This dosed liquid may contain initiators and/or surfactants or the initiator and/or the surfactant may be dosed parallel.

Alternatively, all monomers can be charged into the reactor, before adding the initiator. This method is often referred to as batch process.

It is also possible to do a combination of both processes, by polymerizing a part of the monomers in the manner of a batch process, and feeding the other part afterwards.

As known to the expert in the field, the type of process and mode of operation can be chosen, to achieve the desired particle size, sufficient dispersion stability, a stable production process and so on.

Emulsifiers which may be used are especially anionic and non-ionic surfactants. The amount of emulsifier used is generally not more than 5% by weight, based on the polymer.

Typical surfactants are for example alkyl sulfates (e.g. sodium dodecyl sulfate), alkyl ether sulfates, dioctyl sodium sulfosuccinate, polysorbates (e.g. polyoxyethylene (20) sorbitan monooleate), nonylphenol ethoxylates (nonoxynol-9) and others.

Besides those initiators conventionally used in emulsion polymerization (e.g. per-compounds, such as ammonium peroxodisulfate (APS) redox systems, such as sodium disulphite-APS-iron can be applied. Also water soluble azo initiators may be applied and/or a mixture of initiators can be used. The amount of initiator is usually between 0.005 to 0.5% by weight, based on the monomer weight.

The polymerization temperature depends on the initiators within certain limits. For example, if APS is used it is advantageous to operate in the range from 60 to 90° C.; if redox systems are used it is also possible to polymerize at lower temperatures, for example at 30° C.

The average particle size of the polymer particles produced in the emulsion polymerization may range from 10 to 1000, 20 to 500 or 50 to 250 nm. The average particle size of the polymer particles may be determined by methods well known to a skilled person for instance by the method of laser diffraction. The particle size may be determined by laser diffraction, using a Mastersizer 2000 (Malvern). The values can be indicated as particle radius rMS [nm], which is half of the median of the volume based particle size distribution d(v,50).

The obtained dispersion can directly be used to prepare the coating suspension, or—in rare cases—be used as coating suspension without even adding further ingredients.

The dispersion can also be dried, preferably by spray drying, freeze drying or coagulation. Thus a solid can be obtained, which offers certain advantages with regard to handling and logistics.

The dried polymerizate may than be transferred into a coating suspension by redispersing the solid in water, e.g. (where required) by the use of a high shear mixer.

The dried polymerizate may also be dissolved in a solvent, e.g. an organic solvent, to prepare a coating solution.

If coating with coating solutions is preferred, the preparation of the polymer by solution polymerization or bulk polymerization may be a good option, too.

Release of the Pharmaceutical or Nutraceutical Active Ingredient

The release according to USP of the pharmaceutical or nutraceutical active ingredient is not more than 10, not more than 8 or not more than 5% under in-vitro conditions at pH 1.2 after 2 hours in 0.1 molar HCl with and without the addition of 20, 30 or 40% (v/v) ethanol.

The release according to USP of the pharmaceutical or nutraceutical active ingredient is at least 50, at least 60, at least 80% under in-vitro conditions at pH 6.8 after 45 or after 60 minutes in buffered medium (phosphate buffered saline, pH 6.8, European Pharmacopoeia 4003200).

The USP (USP=United States Pharmacopoeia) which may be preferably used is USP32/NF27 (NF=National Formulary), apparatus II, paddle method, 50 rpm for tablets or paddle or basket method 50 to 100 rpm, depending on the monograph, for pellets.

Further Characteristics of the (Meth)Acrylate Copolymer

The (meth)acrylate copolymer may be characterized by a mean glass transition temperature from 10 to 120 or 20 to 100, preferably 25 to 80° C. (determined by DSC according to DIN EN ISO 11357).

The (meth)acrylate copolymer may be characterized by a minimum film forming temperature of 75° C. or less, preferably 50° C. or less (determined according to DIN ISO 2115).

The (meth)acrylate copolymer may be characterized by a mean molecular weight $M_w$ is 90,000 or more (determined by gel permeation chromatography (GPC).

Core Comprising the Pharmaceutical or Nutraceutical Active Ingredient

The core comprises one or more pharmaceutical or nutraceutical active ingredients as the core or as a part of the core. The one or more pharmaceutical or nutraceutical active ingredients may be more or less homogeneously distributed in a matrix structure within the core structure or may form the core as a crystallized structure. The one or more pharmaceutical or nutraceutical active ingredients may alternatively be present as a part of the core in the form of a layer onto a carrier pellet. Thus the core is an unfinished, coated or uncoated, but still to be coated pharmaceutical or nutraceutical dosage form.

The core, respectively the pharmaceutical or nutraceutical dosage form to be coated by the coating composition may comprise or may contain a neutral carrier pellet, for instance a sugar sphere or non-pareilles, on top of which the active ingredient is bound in a binder, such as lactose or polyvinyl pyrrolidon.

The core may alternatively comprise a pellet in the form of a polymeric matrix in which the active ingredient is bound. The core may comprise an uncoated pellet consisting of a crystallized active ingredient. The core may also comprise its own coating for instance a sustained release coating. Such an already coated core may then be coated by the coating composition described herein.

The core may be uncoated or may comprise a coating, which is different from the coating derived from coating composition described herein. The core may be a coated pellet, for instance with a sustained release coating, an uncoated or coated tablet, an uncoated or coated mini tablet or an uncoated or coated capsule. The core may also comprise a so called "sub coat" as an outer layer.

The core comprises at least more than 80, more than 90, more than 95, more than 98, preferably 100% of the total amount of one or more pharmaceutical or nutraceutical active ingredients present in the gastric resistant pharmaceutical or nutraceutical dosage form.

In some cases it may be useful that the coating composition may comprise, additionally to the active ingredient present in the core, a partial amount, preferably less than 20, less than 10, less than 5 less than 2% by weight of the total amount of one or more pharmaceutical or nutraceutical active ingredients, for instance in order to provide an initial dose of the active ingredient. In this case the coating composition has the function as a binding agent or as a binder for the additional active ingredient. Preferably the coating composition comprises any active ingredient.

Pharmaceutical or Nutraceutical Active Ingredients

The term "a pharmaceutical or nutraceutical active ingredient" shall have the meaning of one or more pharmaceutical or nutraceutical active ingredients. Thus mixtures of different pharmaceutical and/or nutraceutical active ingredients are included in the definition.

Nutraceutical Active Ingredients

The invention is preferably useful for nutraceutical dosage forms.

Nutraceuticals can be defined as extracts of foods claimed to have medical effects on human health. The nutraceutical is usual contained in a medical format such as capsule, tablet or powder in a prescribed dose. Examples for nutraceutical active ingredients are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or antocyanins from berries. Sometimes the expression neutraceuticals is used as synonym for nutraceuticals.

The gastric resistant pharmaceutical or nutraceutical composition is comprising a core, comprising a pharmaceutical or nutraceutical active ingredient. The pharmaceutical or nutraceutical active ingredient may be a pharmaceutical or nutraceutical active ingredient which may be inactivated under the influence of gastric fluids at pH 1.2 or a pharmaceutical or nutraceutical active ingredient which may irritate the stomach mucosa when set free in the stomach.

Pharmaceutical Active Ingredients

The invention is also preferably useful for enteric coated pharmaceutical dosage forms.

Preferred drug classes are those (including but not limited to) coming from parenteral to oral switch considerations and/or high potency drugs (e.g. cytostatics, hormons, hormon receptor agonists, hormon receptor antagonists) and/or drugs with high side effects and toxicity issues (including prodrug metabolization; e.g. peptides, peptidomimetics, nucleotides, nucleosides, nucleoside analogues, taxoids)

Especially preferred are the following drugs

Remicade® (Infliximab, Johnson & Johnson, Schering-Plough, Mitsubishi Tanabe Pharma—Crohn's disease, Rheumatoid arthritis),
Enbrel® (Etanercept, Wyeth—Rheumatoid arthritis),
Zyprexa® (Olanzapine, Eli Lilly and Company—Psychosis),
Seroquel® (Quetiapine, AstraZeneca—Schizophrenia),
Herceptin® (Trastuzumab, Roche, Genentech, Chugai Pharmaceutical—Breast cancer),
Lexapro®, Cipralex® (Escitalopram, Forest Laboratories, H. Lundbeck—Depression, Anxiety disorders),
Gleevec®, Glivec (Imatinib, Novartis—Leukemia),
Avastin® (Bevacizumab, Roche, Genentech—Colorectal cancer),
Taxotere® (Docetaxel, Sanofi-Aventis—Cancer),
Eloxatin®, Eloxatine® (Oxaliplatin, Sanofi-Aventis—Colorectal cancer),
Wellbutrin® (Bupropion, GlaxoSmithKline, Biovail—Depression, Seasonal affective disorder (SAD)),
Abilify® (Aripiprazole, Otsuka Pharmaceutical, Bristol-Myers Squibb—Psychosis, Depression),
Avonex® (Interferonbeta-1a, Biogen Idec—Multiple sclerosis),
Viagra® (Sildenafil, Pfizer—Erectile dysfunction),
Lupron®, Leuplin (Leuprolide, Takeda Pharmaceutical, TAP Pharmaceuticals—Prostate cancer),
Zofran® (Ondansetron, GlaxoSmithKline—Nausea and vomiting),
Arimidex® (Anastrozole, AstraZeneca—Breast cancer),
Prograf® (Tacrolimus, Astellas Pharma—Transplant rejection),
CellCept® (Mycophenolatemofetil, Roche, Chugai Pharmaceutical—Transplant rejection),
Gemzar® (Gemcitabine, Eli Lilly and Company—Cancer),
Cymbalta® (Duloxetine, Eli Lilly and Company—Depression, Anxiety disorders),
Duragesic® (Fentanyl, Johnson & Johnson—Pain),
Casodex® (Bicalutamide, AstraZeneca—Prostate cancer),
Truvada® (Tenofovir+Emtricitabine, Gilead Sciences—HIV infection),
Flomax® (Tamsulosin, Boehringer Ingelheim—Benign prostatic hypertrophy),
Lyrica® (Pregabalin, Pfizer—Neuropathic pain),
Paxil®, Seroxat® (Paroxetine, GlaxoSmithKline—Depression, Anxiety disorders),
Kaletra® (Lopinavir, Abbott Laboratories—HIV infection),
Erbitux® (Cetuximab, Bristol-Myers Squibb, Merck KGaA—Colorectal cancer),
Zoladex® (Goserelin, AstraZeneca—Prostate cancer),
Combivir® (Lamivudine+Zidovudine, GlaxoSmithKline—HIV infection),
Clalis® (Tadalafil, Eli Lilly and Company, Lilly Icos—Erectile dysfunction),
Reyataz® (Atazanavir, Bristol-Myers Squibb—HIV infection),
Concerta® (Methylphenidate, Johnson & Johnson—Attention-deficit hyperactivity dorder),
Camptosar® (Irinotecan, Pfizer—Colorectal cancer),
Adderall® (Amphetamine, Shire Pharmaceuticals—Attention-deficit hyperactivity disorder),
Ultane®, Sevorane® (Sevoflurane, Abbott Laboratories—Anesthesia),
Xeloda® (Capecitabine, Roche, Chugai Pharmaceutical—Cancer),
Femara® (Letrozole, Novartis, Chugai Pharmaceutical—Breast cancer),
Viread® (Tenofovir, Gilead Sciences—HIV infection),
Tarceva® (Erlotinib, Roche, Genentech—Non-small cell lung cancer),
Alimta® (Pemetrexed, Eli Lilly and Company—Non-small cell lung cancer),
Actiq® (Fentanyl, Cephalon—Cancer pain),
Lidoderm® (Lidocaine, Endo Pharmaceuticals—Pain),
Taxol® (Paclitaxel, Bristol-Myers Squibb—Cancer),
Trizivir® (Abacavir+Lamivudine+Zidovudine, GlaxoSmithKline—HIV infection),
Epzicom®, Kixeva® (Abacavir+Lamivudine, GlaxoSmithKline—HIV infection),
Venlafaxine® (Effexor, Wyeth—Antidepressant)
. . . as well as drugs of the respective compound class thereof and/or the respective mode of action implied by said examples (as the latter is a descriptor of not only the physico-chemistry of the active pharmaceutical ingredient (API) but also its physiological behaviour and pharmaceutical character).

Therapeutical and chemical classes of drugs used in enteric coated pharmaceutical dosage forms are for instance analgetics, antibiotics or anti-infectives, antibodies, antiepileptics, antigens from plants, antirheumatics, betablocker, benzimidazole derivatives, beta-blocker, cardiovascular drugs, chemotherapeuitcs, CNS drugs, digitalis glycosides, gastrointestinal drugs, e.g. proton pum inhibitors, enzymes, hormons, liquid or solid natural extracts, oligonucleotides, peptidhormon proteins, therapeutical bacteria, peptides, proteins, proton pump inhibitors, (metal)salt f.e. aspartates, chlorides, orthates, urology drugs, vaccines Examples of drugs, which are acid-lablile, irritating or need controlled release, may be: Acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin, progabide, prosomatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof. Other examples of suitable pharmaceutical or nutraceutical active ingredients are diprophylline, metoprolol succinate and cytidine (as a model substance for nucleoside molecules and their analogues respectively).

Pharmaceutical or Nutraceutical Excipients

The gastric resistant coating layer may comprise, essentially comprise or contain up to 70, up to 60, up to 50, up to 40, up to 30, up to 20% by weight or any pharmaceutical or nutraceutical excipients.

Pharmaceutical or nutraceutical excipients may be selected from the group of antioxidants, brighteners, binding agents, flavouring agents, flow aids, fragrances, glidants, penetration-promoting agents, pigments, plasticizers, polymers, which are different from the (meth)acrylate copolymer of the gastric resistant coating layer as claimed in claim 1, pore-forming agents or stabilizers.

Addition of Further Polymers to the Gastric Resistant Coating Layer

The gastric resistant coating layer may further comprise, essentially comprise or contain optionally 0 to 70, 0 to 60, 0 to 50, 0 to 40, 0 to 30, 0 to 20, 0 to 10% by weight or any of one or more polymers which are different from (meth) acrylate copolymers comprising polymerized units of
10 to 40% by weight of acrylic or methacrylic acid
10 to 80% by weight of a $C_4$- to $C_{18}$-alkyl ester of acrylic or methacrylic acid and optionally
0 to 60% by weight of another vinylic monomer.

Such further polymers may be for instance water-insoluble polymers.

The further polymers are preferably added separately to the coating suspension. These further polymers are not prepared together with the (meth)acrylate copolymer as described above in a single emulsion polymerization process as a core/shell polymerizate.

Water-insoluble Polymers

Water-insoluble polymers are polymers which do not dissolve in water or are only swellable in water over of the whole range of pH 1-14. Water-insoluble polymers may be at the same time polymers containing not more than 12% of monomer residues with ionic side groups, like for instance EUDRAGIT® NE/NM or EUDRAGIT® RL/RS polymers.

The one or more water-insoluble polymers or one may preferably contain less than 10% by weight of monomer residues with ionic side groups, preferably not more than 12% by weight of monomer residues with cationic side groups.

The one or more water-insoluble polymers or one or more cellulosic polymers may preferably contain less than 5% by weight, preferably not more than 2% by weight, more preferably not more than 1 or 0.05 to 1% by weight, of monomer residues with anionic side groups.

Other kinds of water-insoluble polymers in the sense of the invention may be vinyl copolymers like polyvinylacetate, including derivates of polyvinylacetate. The polyvinylacetate may be present in the form of a dispersion. One example is the type Kollicoat® SR 30 D (BASF), polyvinylacetate dispersion, stabilized with povidone and sodium laurylsulfate.

The water-insoluble polymers may preferably belong to the group of (meth)acrylate copolymers.

EUDRAGIT® NE 30D/EUDRAGIT® NM 30D—Type Polymers

The gastric resistant coating layer may comprise a water-insoluble copolymer which is a copolymer composed of free-radical polymerized units of more than 90% by weight, or more than 95% by weight, in particular to an extent of at least 98% by weight, preferably to an extent of at least 99% by weight, in particular to an extent of at least 99% by weight, more preferably to an extent of 100% by weight, of (meth)acrylate monomers with neutral moieties, especially $C_1$- to $C_4$-alkyl moieties. These kinds of polymers do not dissolve in water or are only swellable in water over of the whole range of pH 1-14.

Suitable (meth)acrylate monomers with neutral moieties are, for example, methyl methacrylate, ethyl methacrylate, n-butyl methacrylate, methyl acrylate, ethyl acrylate, n-butyl acrylate. Preference is given to methyl methacrylate, ethyl acrylate and methyl acrylate.

Methacrylate monomers with anionic moieties, for example acrylic acid and/or methacrylic acid, may be present in small amounts of less than 5% by weight, preferably not more than 2% by weight, more preferably not more than 1 or 0.05 to 1% by weight.

Suitable examples are neutral or virtually neutral (meth) acrylate copolymers composed of 20 to 40% by weight of ethyl acrylate, 60 to 80% by weight of methyl methacrylate and 0 to less than 5% by weight, preferably 0 to 2 or 0.05 to 1% by weight of methacrylic acid or any methacrylic acid (EUDRAGIT® NE 30D or EUDRAGIT® NM 30D type).

EUDRAGIT® NE 30D and Eudragit® NM 30D are dispersions containing 30% by weight of copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM 30D type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

EUDRAGIT® RL/RS-Type Polymers

The gastric resistant coating layer may comprise a water-insoluble copolymer which is a copolymer composed of free-radical polymerized units of 85 to 98% by weight of free-radical polymerized $C_1$ to $C_4$ alkyl esters of acrylic or methacrylic acid and 15 to 2% by weight of (meth)acrylate monomers with a quaternary amino group in the alkyl moiety. These kinds of polymers do not dissolve in water or are only swellable in water over of the whole range of pH 1-14.

Coating

Coating suspensions may be applied by spray or powder coating processes following known processes. As a rule the coated compositions may be cured at elevated temperatures for example 24 hours at 40° C. or 60° C. after the spray coating in order to provide reproducible and stable functionality.

The polymer dry weight gain of the coating layer may be at least 2.5, at least 3.5, at least 4, preferably 4 to 30, preferably 4 to 20, more preferably 5 to 18, or most preferably 10 to 18 mg/cm² surface area. This may correlate to 2-60% polymer dry weight gain related to the weight of the core. In the case of coated tablets the polymer dry weight gain related to the weight of the core (tablet core: around 1-25 or 1-10 mm in diameter or length) may be 2-30%. In the case of coated pellets the polymer dry weight gain related to the weight of the core (pellet core: 0.1 to 1.5 mm in diameter) may be 10-60%.

Pellets are typically coated with at least 4 weight % of polymer, based on the weight of the uncoated pellets (i.e. 4% polymer weight gain). A better protection of the active ingredient is achieved with a thicker coating of 6%, 8% or 10% polymer weight gain. Usually not more than 40% polymer weight gain of coating are applied to pellets, as then the time for the dissolution of the coating layer starts getting too long. In many cases less than 30%, less than 25%, or less than 20% polymer weight gain are sufficient.

On tablets and capsules, a coating with typically at least 2 mg polymer per cm² of surface is applied. In most cases at least 3 mg, 4 mg or 6 mg of polymer per cm² of surface are applied. Coating amounts of more than 40 mg of polymer per cm² of surface are hardly ever used; typically less than 30 mg, less than 25 mg or less than 20 mg of polymer per cm² of surface are applied.

In general more coating thickness is required for capsules and oblong shaped tablets, while more spherical dosage forms require less coating.

Top Coat and Sub Coats

The gastric resistant pharmaceutical or nutraceutical composition according to the invention may be further coated with a sub coat or a top coat or both.

A sub coat may be located between the core and the gastric resistant (enteric) coating layer. A sub coat may have the function to separate substances of the core from substances of the controlling layer which may be incompatible with each other. The sub coat has essentially no influence on the active ingredient release characteristics. A subcoat is preferably essentially water-soluble, for instance it may consist of substances like hydroxypropylmethyl-cellulose (HPMC) as a film former. The average thickness of the subcoat layer is very thin, for example not more than 15 μm, preferably not more than 10 μm.

A top coat is also preferably essentially water soluble. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

The expressions sub coat and top coat are well known to the person skilled in the art.

Use

The invention is also discloses the use of the (meth) acrylate copolymer as defined herein in the gastric resistant coating layer of an ethanol resistant, gastric resistant pharmaceutical or nutraceutical composition, comprising a core, comprising a pharmaceutical or nutraceutical active ingredient and a gastric resistant coating layer onto the core, wherein the gastric resistant coating layer comprises, essentially comprises or contains at least 30, at least 40, at least 50, at least 60, at least 70, at least 80, at least 90 or 100% by weight of the (meth)acrylate copolymer, whereby the ethanol resistant, gastric resistant pharmaceutical or nutraceutical composition shows a release of the pharmaceutical or nutraceutical active ingredient of not more than 10, not more than 8 or not more than 5% under in-vitro conditions at pH 1.2 after 2 hours in medium according to USP with and without the addition of 20, 30 or 40% (v/v) ethanol.

Likewise as described in WO2008/049657 the (meth) acrylate copolymer compositions as described herein may be useful as binding agents and matrix formers for active ingredients included in retarded or sustained release oral dosage forms in order to minimize the effect of acceleration or deceleration of the active ingredient release by the influence of ethanol under in-vitro conditions.

EXAMPLES

Abbreviations:
EA=ethyl acrylate
MMA=methyl methacrylate
n-BuMA=n-butyl methacrylate
EHMA=2-ethylhexyl methacrylate
i-DMA=isodecyl methacrylate
LMA=lauryl methacrylate
MAS=methacrylic acid
TGEH=thioglcolic acid-2-ethylhexyl-ester
n.d.=not determined
(C)=comparative example Preparation of a Polymer Dispersion, According to the Invention The polymer is prepared in a 1 liter round bottom flask, equipped with a lid, an anchor stirrer, a baffle, a reflux condenser, a feed pipe for nitrogen and a temperature probe to monitor the temperature inside the reactor. A water bath with a thermostat is used to control the reaction temperature.

653 g of deionized water, 13.2 g of sodium dodecylsulfate solution (15% in water; Disponil SDS 15) and 6.5 g of polysorbate 80 (TEGO SMO 80V) were charged into the flask. The reactor was flushed with nitrogen and the mixture was agitated with the stirrer and heated to a starting temperature of 82° C.

In a separate flask, a stable monomer emulsion is prepared from 280.0 g of monomers (monomer composition in weight-% according to table) and 9 g deionized water.

0.8 g of thioglycolic acid 2-ethylhexyl ester (TGEH; 0.3 weight-% based on the total amount of monomers) were added to the monomer mixture as chain transfer agent. (Deviating hereof, in example 7) 0.3 g of thioglycolic acid 2-ethylhexyl ester (0.1 weight-%) and in example 8) 1.7 g of thioglycolic acid 2-ethylhexyl ester (0.6 weight-%) were added)

Again in a separate flask, 0.12 mol % (with regard to the sum of used monomers) ammonium persulfate are dissolved in 5 g of deionized water (initiator solution).

When the temperature inside the reactor has reached 82° C., the initiator solution is added to the reactor. Two minutes later, the dosing of the monomer emulsion is started at a dosing rate of 2 g/min. By adjusting the temperature of the water bath, the temperature inside the reactor is kept at 82° C. After all the monomer emulsion is added, the temperature is kept for another 30 minutes at 82° C. Then, the reactor content was allowed to cool down to 20° C. and was filtered through a 250 µm gaze.

Preparation of a Spraying Suspension (Samples 1-12 and 14)

1.8 g of triethyl citrate, 9.0 g of talkum and 73.2 g deionized water were charged into a vessel and homogenized for 15 minutes with an ULTRA TURRAX high-performance dispersing instrument.

60.0 g of the polymer dispersion (30% solids content) is stirred with a magnetic stirrer. After the talcum dispersion is slowly poured into to polymer dispersion, the stirring is continued for 60 minutes, before the mixture is filtered through a 240 µm gaze.

(The coating suspension is about 1.5 times the amount needed for the described coating process. The amount needed is determined by the polymer weight gain of 8% as indicated in the spraying process section.)

Preparation of a Spraying Suspension (Samples 13)

8.8 g of triethyl citrate, 210.0 g of micronized talcum and 1057 g deionized water were charged into a vessel and homogenized for 15 minutes with an ULTRA TURRAX high-performance dispersing instrument.

350.0 g of the polymer dispersion (30% solids content) is stirred with a magnetic stirrer. After the talcum dispersion is slowly poured into to polymer dispersion, the stirring is continued for 60 minutes, before the mixture is filtered through a 240 µm gaze. The spray suspension was prepared analogous to the spray suspension of samples 1-12.

(The coating suspension is about 1.5 times the amount needed for the described spraying process. The amount needed is determined by the polymer weight gain of 17.5% as indicated in the spraying process section.)

Spraying Process (Samples 1-12)

A MicroLab coater (Oystar Hüttlin) was used to prepare the coatings.

150 g of Diprophylline pellets (diameter 0.8-1.0 mm, 55% active content) were charged into the MicroLab instrument and agitated with low air supply.

The fluid bed temperature was raised to 23-25° C. and the pellets were coated within 1 hour up to a polymer weight gain of 8% (additional weight due to polymer in coating with respect to initial pellets' weight). The spray rate was raised slowly to a maximum of 2 g/min.

After the coating process, the pellets were agitated in the instrument for another 5 minutes for additional drying and curing. Then the coated pellets were allowed to cool down in the instrument with low air supply. The cold pellets were strewed with small amounts of talkum, to prevent sticking and tempered for 2 hours at 40° C.

Spraying Process (Samples 13)

A MicroLab coater (Oystar Within) was used to prepare the coatings.

350 g of metoprolol succinate pellets (diameter 0.7-1.0 mm, 20% active content) were charged into the MicroLab instrument and agitated with low air supply.

The fluid bed temperature was raised to 23-26° C. and the pellets were coated within 2.5 hour up to a polymer weight gain of 17.5% (additional weight due to polymer in coating with respect to initial pellets' weight). The spray rate was raised slowly to a maximum of 2 g/min.

After the coating process, the pellets were agitated in the instrument for another 5 minutes for additional drying and curing. Then the coated pellets were allowed to cool down in the instrument with low air supply.

Examples 1 to 12a

In examples 1 to 12a Diprophylline pellets (average diameter 0.8 to 1.0 mm) were coated.

Examples 8 and 11 are comparative (C) examples

Example 12b

In example 12b Diprophylline pellets (average diameter 0.8 to 1.0 mm) were coated. However Example 12b differs from example 12a by the polymer proportion, which consisted of 66.6% by dry weight of the polymer as described for example 12a, b in table 1 and 33.3% by dry weight of a neutral (meth)acrylate copolymer consisting of polymerized units of 70% by weight methyl methacrylate and 30% by weight of ethyl acrylate (EUDRAGIT® NM 30D).

Example 13

In example 13 Metoprolol Succinate pellets (average diameter 0.85 to 1.0 mm) were coated. The polymer proportion consisted of 32% by dry weight of the polymer as described for example 13 in table 1 and 68% by dry weight of a neutral (meth)acrylate copolymer consisting of polymerized units of 70% by weight methyl methacrylate and 30% by weight of ethyl acrylate (EUDRAGIT® NM 30D). The spray suspension contained 10% by weight of triethylcitrate and 200% by weight of talc based on the weight of the total polymer content.

Active Ingredient Layering and Enteric Coating Process

Example 14

A MicroLab coater (Oystar Within) was used to prepare the coatings.

150 g of cellulose pellets (Cellets® 700; diameter 700-1000 µm) were charged into the MicroLab instrument and agitated with low air supply.

For the layering of the active, a solution of 90 mL of deionized water, 7.5 g of polyvinylpyrollidone (PVP; Kollidon® K25) and 1.5 g of Cytidine was prepared and homogenized for 10 minutes with a high-shear mixer.

The fluid bed temperature was raised to 30° C. and then the pellets were coated slowly within 4 hours with the layering solution. During the coating process, the spray rate was raised gently to a maximum of 0.8 g/min. Upon completion of the coating, the pellets were agitated in the instrument for another 5 minutes for additional drying and curing. After the coating, the resulting pellets had an active content of around 1%.

Spraying Process (Sample 14)

A MicroLab coater (Oystar Within) was used to prepare the coatings.

150 g of the Cytidine pellets (diameter 700-1000 µm, 1% active content) were charged into the MicroLab instrument and agitated with low air supply.

The fluid bed temperature was raised to 26-27° C. and the pellets were coated within 2 hours up to a polymer weight gain of 8% (additional weight due to polymer in coating with respect to initial pellets' weight). The spray rate was raised slowly to a maximum of 1.2 g/min.

After the coating process, the pellets were agitated in the instrument for another 5 minutes for additional drying and curing. Then the coated pellets were allowed to cool down in the instrument with low air supply. The cold pellets were strewed with small amounts of talkum, to prevent sticking and tempered for 2 hours at 40° C.

Analytical Methods

Particle Size rMS [nm]

The particle size was determined by laser diffraction, using a Mastersizer 2000 (Malvern).

The values are indicated as particle radius rMS [nm], which is half of the median of the volume based particle size distribution d(v,50).

Viscosity Number Vz [mL/g]

The viscosity number Vz is often used as a measure for the molecular weight. It was determined in accordance with DIN EN ISO 1628-1.

A process controlled viscosity measuring system (PVS, Lauda GmbH & Co. KG) with an Ubbelohde capillary (type Oc) was used.

The polymer was dissolved in THF, at a concentration of 0.5 g per 100 mL of solvent.

The temperature of the measurement was 25° C.

Molecular Weight Mw [g/mol]

The molecular weight was determined by gel permeation chromatography (GPC).

The molar mass calibration was based on poly(methyl methacrylate).

The conditions of the measurement were chosen according to the publication of Martina Adler et.al. (e-Polymers 2004, 055).

N,N-Dimethylacetamide with 6 g/L acetic acid, 3 g/L LiBr and 10 g/L $H_2O$ was used as a mobile phase, with a flow rate of 1.0 ml/min. A column set of 4 GRAM 10 μm columns (precolumn, 2×10.000 Å and 30 Å column—Polymer Standards Service, Mainz, Germany) was used as stationary phase.

Glass Transition Temperature Tg [° C.]

The glass transition temperature Tg was determined by DSC according to DIN EN ISO 11357. Typically between 10 and 12 mg sample, and a heating rate of 20 K/min was used; the temperature range was −40° C. to 140° C. The measurement is carried out under nitrogen atmosphere. The evaluation was based on the second heating cycle, and the indicated value is the mean value in the glass transition interval.

Minimum Film-forming Temperature MFT [° C.]

The lowest temperature at which a polymer-dispersion will form a polymer film upon evaporation of the water is the minimum film-forming temperature (MFT). The MFT is characteristic of the dispersion and is—amongst others—influenced by the glass transition temperature and the particle size of the dispersed particles.

The minimum film-forming temperature has been determined according to DIN ISO 2115 by applying the dispersion with a doctor knife on a band heater at a defined temperature gradient. The MFT corresponds to the lowest temperature at which a crack-free film is formed and is slightly above the whitening point (which is the temperature at which the polymer still appears whitish because the film has not yet fully been formed).

Active Ingredient Release

The release properties were determined in a dissolution apparatus (USP 32 <711> dissolution; type 1: basket), at a rotation speed of 100 rpm, with 900 mL of dissolution medium. The temperature was 37° C.±0.5° C.

The dissolution medium was 0.1 N hydrochloric acid (0.1 N HCl) for 2 hours; then a full exchange of the dissolution medium to pH 6.8 EP-buffer 4003200 was done.

The amount of released API (diprophylline, metoprolol succinate or cytidine, respectively) was determined by UV-measurements.

The effect of ethanol was studied by replacing a part of the hydrochloric acid with ethanol. Measurements with 10% ethanol (by volume), 20% ethanol (by volume), 30% ethanol (by volume) and/or 40% ethanol (by volume) were carried out.

The dissolution medium after the full exchange to pH 6.8 did not contain any ethanol (in all cases).

TABLE 1

Monomer compositions

| Example No. | EA | MMA | n-BuMA | EHA | EHMA | i-DMA | LMA | MAS | +TGEH (weight-% based on total monomer weight) |
|---|---|---|---|---|---|---|---|---|---|
| 1 | 30.0 | | | | 40.0 | | | 30.0 | 0.3 |
| 2 | 30.0 | | | 40.0 | | | | 30.0 | 0.3 |
| 3 | 25.0 | 5.0 | | 40.0 | | | | 30.0 | 0.3 |
| 4 | 40.0 | | 30.0 | | | | | 30.0 | 0.3 |
| 5 | 40.0 | | | | | 30.0 | | 30.0 | 0.3 |
| 6 | 40.0 | | | | | | 30.0 | 30.0 | 0.3 |
| 7 | 40.0 | | | 30.0 | | | | 30.0 | 0.1 |
| 8 (C) | 40.0 | | | 30.0 | | | | 30.0 | 0.6 |
| 9 | 23.7 | | | 51.3 | | | | 25.0 | 0.3 |
| 10 | 21.8 | | | 60.1 | | | | 18.1 | 0.3 |
| 11 (C) | 63.2 | | | | | | | 36.8 | 0.3 |
| 12a, b | 27.2 | | | 57.1 | | | | 15.7 | 0.3 |
| 13 | 23.7 | | | 51.3 | | | | 25.0 | 0.3 |
| 14 | 31.3 | — | — | — | 44.4 | — | — | 24.0 | 0.3 |

TABLE 2

Characteristics of the polymers

| Example No. | rMS [nm] | VZ [mL/g] | Mw [g/mol] | Tg [° C.] | MFT [° C.] |
|---|---|---|---|---|---|
| 1 | 49 | 47.8 | 141000 | 70 | 47.5 |
| 2 | 49 | 85.3 | 312000 | 42 | 13.5 |

TABLE 2-continued

Characteristics of the polymers

| Example No. | rMS [nm] | VZ [mL/g] | Mw [g/mol] | Tg [° C.] | MFT [° C.] |
|---|---|---|---|---|---|
| 3 | 53 | 67.2 | 285000 | 47 | 23.5 |
| 4 | 49 | 67.5 | 255000 | 75 | 33.5 |
| 5 | 51 | 70.0 | 262000 | 57 | 29.5 |
| 6 | 56 | 62.0 | 233000 | 59 | 17.5 |
| 7 | 48 | n.d. | 561000 | 66 | 30.0 |
| 8 (C) | 49 | n.d. | 81700 | 70 | 29.5 |
| 9 | 51 | 36.1 | 112000 | 55 | 46.0 |
| 10 | 50 | n.d. | 99900 | 26 | <0 |
| 11 (C) | 49 | 77.6 | 300000 | 58 | <0 |
| 12a | 48 | n.d. | 111000 | 28 | n.d. |
| 13 | 51 | n.d. | 117000 | 47 | n.d. |
| 14 | 51 | n.d. | 124000 | 56 | n.d. | n.d. = not determined

TABLE 3

Active ingredient release at pH 1.2

| Example No. | Dissolution-pH | 0% EtOH | 10% EtOH | 20% EtOH | 30% EtOH | 40% EtOH |
|---|---|---|---|---|---|---|
| 1 | 6.8 | 0.70 | 0.50 | 0.93 | 25.91 | 82.09 |
| 2 | 6.1 | 0.22 | 0.50 | 3.47 | 19.32 | 70.24 |
| 3 | 6.5 | 0.13 | 0.16 | 2.14 | 15.03 | 73.51 |
| 4 | 6.8 | 1.35 | 0.54 | 3.06 | 61.66 | 87.38 |
| 5 | 6.3 | 1.54 | n.d. | 2.72 | 0.37 | 75.92 |
| 6 | 5.9 | 2.56 | 3.67 | n.d. | 2.23 | 80.58 |
| 7 | 6.7 | 0.12 | n.d. | 1.35 | 64.93 | 89.25 |
| 8 (C) | 6.7 | 0.18 | n.d. | 15.72 | 58.11 | 73.15 |
| 9 | 6.8 | 0.70 | n.d. | 0.53 | 1.95 | 67.64 |
| 10 | 7.0 | n.d. | n.d. | 0.35 | 1.05 | 7.32 |
| 11 (C) | 5.9 | 4.40 | n.d. | 78.31 | 99.43 | 99.78 |
| 12a | 7.1 | 0.14 | n.d. | n.d. | 2.71 | 10.67 |
| 12b | n.d. | 0.28 | n.d. | 0.64 | 4.59 | 28.43 |
| 13 | 7.1 | 0.00 | n.d. | 0.57 | 0.00 | 1.00 |
| 14 | n.d. | 0.95 | n.d. | n.d. | 7.96 | n.d. | n.d. = not determined

The invention claimed is:

1. A gastric resistant pharmaceutical or nutraceutical composition, comprising:
   a core comprising a pharmaceutical or nutraceutical active ingredient; and
   a gastric resistant coating layer onto the core,
   wherein the gastric resistant coating layer comprises at least 30% by weight of a (meth)acrylate copolymer, wherein the (meth)acrylate copolymer consists of polymerized units of
   from 10 to 40% by weight of acrylic or methacrylic acid,
   from 10 to 50% by weight of ethyl acrylate,
   from 10 to 80% by weight of a $C_4$ to $C_{18}$-alkyl ester of acrylic or methacrylic acid, and
   optionally from 0 to 20% by weight of methyl methacrylate,
   wherein the (meth)acrylate copolymer has a mean molecular weight $M_w$ of 90,000 or more,
   wherein the pharmaceutical or nutraceutical active ingredient is released not more than 10% under an in-vitro condition at pH 1.2 after 2 hours in a media according to USP with and without an addition of 20% ethanol, and wherein the pharmaceutical or nutraceutical active ingredient is released at least 50% under an in-vitro condition at pH 6.8 after 45 minutes in a buffered media according to USP.

2. The gastric resistant pharmaceutical or nutraceutical composition according to claim 1, wherein the (meth)acrylate copolymer has a mean glass transition temperature of from 25 to 80° C.

3. The gastric resistant pharmaceutical or nutraceutical composition according to claim 1,
   wherein the (meth)acrylate copolymer has a minimum film forming temperature of 50° C. or less.

4. The gastric resistant pharmaceutical or nutraceutical composition according to claim 1,
   wherein the $C_4$- to $C_{18}$-alkyl ester of acrylic or methacrylic acid are selected from the group consisting of n-butyl methacrylate, 2-ethylhexyl acrylate, 2-ethylhexyl methacrylate, isodecyl methacrylate, and lauryl methacrylate.

5. The gastric resistant pharmaceutical or nutraceutical composition according to claim 1,
   wherein the (meth)acrylate copolymer consists of polymerized units of
   from 20 to 40% by weight of the methacrylic acid,
   from 20 to 40% by weight of n-butyl methacrylate, and
   from 30 to 50% by weight of ethyl acrylate.

6. The gastric resistant pharmaceutical or nutraceutical composition according to claim 1,
   wherein the (meth)acrylate copolymer consists of polymerized units of
   from 20 to 40% by weight of the methacrylic acid,
   from 30 to 50% by weight of 2-ethylhexyl acrylate,
   from 15 to 40% by weight of ethyl acrylate, and
   optionally from 0 to 20% by weight of methyl methacrylate.

7. The gastric resistant pharmaceutical or nutraceutical composition according to claim 1,
   wherein the (meth)acrylate copolymer consists of polymerized units of
   from 10 to 40% by weight of the methacrylic acid,
   from 20 to 70% by weight of 2-ethylhexyl methacrylate, and
   from 10 to 50% by weight of ethyl acrylate.

8. The gastric resistant pharmaceutical or nutraceutical composition according to claim 7,
   wherein the (meth)acrylate copolymer consists of polymerized units of
   from 20 to 40% by weight of the methacrylic acid,
   from 20 to 50% by weight of the 2-ethylhexyl methacrylate, and
   from 20 to 50% by weight of the ethyl acrylate.

9. The gastric resistant pharmaceutical or nutraceutical composition according to claim 7,
   wherein the (meth)acrylate copolymer consists of polymerized units of
   from 10 to 35% by weight of the methacrylic acid,
   from 40 to 70% by weight of the 2-ethylhexyl methacrylate, and
   from 10 to 30% by weight of the ethyl acrylate.

10. The gastric resistant pharmaceutical or nutraceutical composition according to claim 1,
    wherein the (meth)acrylate copolymer consists of polymerized units of
    from 20 to 40% by weight of the methacrylic acid,
    from 20 to 40% by weight of isodecyl methacrylate, and
    from 40 to 50% by weight of ethyl acrylate.

11. The gastric resistant pharmaceutical or nutraceutical composition according to claim 1,
    wherein the (meth)acrylate copolymer consists of polymerized units of
    from 20 to 40% by weight of the methacrylic acid,
    from 20 to 40% by weight of lauryl methacrylate, and
    from 30 to 50% by weight of ethyl acrylate.

12. The gastric resistant pharmaceutical or nutraceutical composition according to claim 1,
wherein the gastric resistant coating layer comprises up to 80% by weight of a pharmaceutical or nutraceutical excipient selected from the group consisting of an antioxidant, a brightener, a binding agent, a flavouring agent, a flow aid, a fragrance, a glidant, a penetration-promoting agent, a pigment, a plasticizer, a polymer, a pore-forming agent, and a stabilizer.

* * * * *